United States Patent [19]
Beavers

[11] Patent Number: 5,945,549
[45] Date of Patent: Aug. 31, 1999

[54] PRODUCTION OF AQUEOUS SOLUTIONS OF MIXTURES OF FORMYLTERTRAHYDROFURAN AND HYDRATES THEREOF

[75] Inventor: William Anthony Beavers, Longview, Tex.

[73] Assignee: Eastman Chemical Company, Kingsport, Tenn.

[21] Appl. No.: 09/235,448

[22] Filed: Jan. 22, 1999

[51] Int. Cl.$^6$ .................................................. C07D 307/12
[52] U.S. Cl. ........................................... 549/483; 549/502
[58] Field of Search ..................... 549/483, 502

[56] References Cited

U.S. PATENT DOCUMENTS

| | | |
|---|---|---|
| 4,215,077 | 7/1980 | Matsumoto et al. . |
| 4,567,305 | 1/1986 | Matsumoto et al. . |
| 4,678,857 | 7/1987 | Dureanleau et al. . |
| 5,138,101 | 8/1992 | Devon . |
| 5,840,928 | 11/1998 | Satoh et al. .............................. 549/483 |

*Primary Examiner*—Bernard Dentz
*Attorney, Agent, or Firm*—Michael J. Blake; Harry J. Gwinnell

[57] ABSTRACT

Disclosed is a process for the recovery of formyltetrahydrofurans (FTHF's) produced by the rhodium-catalyzed hydroformylation of 2,5-dihydrofuran (2,5-DHF) wherein the FTHF's are recovered as an equilibrium mixture of 2- & 3-FTHF and their hydrates, 2- and 3-[di(hydroxy)methyl] tetrahydrofuran from a hydroformylation product solution comprising a rhodium catalyst, 2- and 3-FTHF and an organic hydroformylation solvent obtained as a liquid product take-off from a hydroformylation process wherein 3-FTHF is produced by the hydro-formylation of 2,5-DHF 3-FTHF is a valuable organic intermediate useful, for example, in the preparation of 3-methyltetrahydrofuran and 3-amino-methyltetrahydorfuran.

3 Claims, No Drawings

PRODUCTION OF AQUEOUS SOLUTIONS OF MIXTURES OF FORMYLTERTRAHYDROFURAN AND HYDRATES THEREOF

This invention pertains to a process for the recovery of formyl-tetrahydrofurans (FTHF's) produced by the rhodium-catalyzed hydroformylation of 2,5-dihydrofuran (2,5-DHF). More specifically, this invention pertains to the production of an equilibrium mixture of 2- and 3-FTHF and their hydrates 2- and 3-[di(hydroxy)methyl]tetrahydrofuran (DHMTHF) from a solution comprising a rhodium catalyst, a phosphine promoter, 2- and 3-FTHF and a hydroformylation solvent obtained as a liquid product take-off from a hydroformylation process wherein 3-FTHF is produced by the hydroformylation of 2,5-DHF. 3-FTHF is a valuable organic intermediate useful in the preparation of a variety of pharmaceutical and agricultural products. More specifically, 3-FTHF provides access to unusual 3-substituted tetrahydrofuran derivatives such as 3-hydroxymethyltetrahydrofuran, 3-methylaminotetrahydrofuran, and 3-methyltetrahydrofuran.

The hydroformylation reaction is well-known in the art as a catalytic method for the conversion of an olefin into an aldehyde product having one carbon more than the starting mono-olefin by the addition of one molecule each of hydrogen and carbon monoxide to the carbon-carbon double bond. Most commercial hydroformylation facilities employ catalyst systems comprising rhodium and organophosphine compounds such as tertiary (trisubstituted), mono- and bisphosphines. For example, U.S. Pat. No. 3,527,809 discloses the hydroformylation of olefins employing a catalyst system comprising rhodium and organophosphorus compounds such as triphenylphosphine (TPP) and reactor pressures below 500 psig. Hydroformylation processes which employ catalyst systems comprising rhodium in combination with other organophosphine compounds and are operated at low to moderate reactor pressures are described in U.S. Pat. No. 3,239,566 (tri-n-butylphosphine) and U.S. Pat. No. 4,873,213 (tribenzylphosphine).

The most extensive use of hydroformylation processes is in the hydroformylation of ethylene and propylene to produce propionaldehyde nd isomeric butyraldehydes. These low-boiling aldehydes may be recovered by means of a gas stripped reactor wherein unreacted gases are used to sweep the aldehyde product as a vapor from the high-boiling reaction mixture contained in the reactor. Such a vapor take-off process is disclosed in U.S. Pat. No. 4,287,369. This method works well for relatively low-boiling aldehyde products because of their relatively high vapor pressure at the temperature at which the hydroformylation process is operated. The method becomes progressively more impractical as the boiling point of aldehyde products increases which requires a substantial increase in the volume of the stripping gas flow in order to remove an equivalent amount of product.

Another traditional product separation technique involves the distillation of the aldehyde product from a high-boiling residue or "heel" containing the catalyst system. For example, U.S. Pat. No. 4,137,240 describes the hydroformylation of cyclic acetals of acrolein using a catalyst system comprising rhodium and triphenylphosphite. The high-boiling products of the disclosed process were separated from the catalyst heel by high-temperature, vacuum distillation, resulting in the formation of metallic rhodium which is especially undesirable since the extremely valuable metallic rhodium can plate out on the surface of the process equipment and be lost from the hydroformylation process.

U.S. Pat. No. 4,533,757 discloses a variation of the above-described vapor stripping relative to the recovery of a high boiling aldehyde, nonanal, from a hydroformylation mixture containing rhodium and triphenylphosphine. According to this patent, a liquid reactor effluent comprising a solution of nonanal, catalyst components and a high-boiling solvent is fed to a low pressure, let-down tank. In this tank, stripping gas from the reactor is sparged up through the catalyst solution to vaporize the aldehyde product and strip it out at the lower pressure. The lower pressure requires less stripping gas than would be required if attempted at the higher pressure within the hydroformylation reactor. This method requires the use of significant amounts of energy in the form of recompression of the low pressure stripping gas for recycle to the reactor.

The following patents refer to the use of distillation procedures in the isolation high-boiling aldehydes produced by the hydroformylation of olefins containing a functional group: U.S. Pat. No. 2,894,038—hydroformylation of 4-formylcyclohexene using a rhodium/cobalt catalyst; U.S. Pat. No. 3,966,827—hydroformylation of 4-hydroxy-2-methylbutene-1; U.S. Pat. No. 4,275,243—recovery of 4-hydroxybutyraldehyde. It is evident from the numerous and varied types of aldehydes mentioned that there is a need for a method of product separation that does not employ the high temperatures that are required to isolate the high-boiling aldehydes by conventional distillation techniques.

A number of different techniques for separating hydroformylation catalysts from aldehydes have been described in the literature. U.S. Pat. Nos. 4,144,191 and 4,262,147 describe the use of specific mixed rhodium/cobalt carbonyl cluster catalysts bound to amine groups on a polymer support. This catalyst was specifically designed for the "one pot" sequential hydroformylation and reduction steps using dicyclopentadiene for conversion into tricyclic dimethanol product. U.S. Pat. No. 4,533,757 discloses that this system loses rhodium from the resin support to the oxo product.

Another approach which has been disclosed in the literature is the use of functionalized, water-soluble, organophosphorus compounds in combination with rhodium. U.S. Pat. No. 3,857,895 discloses the use of aminoalkyl and aminoaryl organophosphine compounds in combination with rhodium. The catalyst solution containing the aldehyde product is extracted with aqueous acid to recover the rhodium and organophosphine catalyst components from an aldehyde-containing, organic solution. Since the acid must be neutralized to recover the catalyst in a form that can be readmitted to the reactor, the process presents salt disposal problems.

There are many patents pertaining to the hydroformylation of allyl alcohol wherein an aqueous extraction has been employed to separate the 4-hydroxybutyraldehyde product from the solution containing the catalyst. This special case reflects the substantial water solubility of both the allyl alcohol feedstock and product 4-hydroxybutyraldehyde. Thus, as disclosed in U.S. Pat. No. 4,215,077, it is important that very high conversions of allyl alcohol, preferably above 95 percent, are achieved in the hydroformylation reactor. Another aspect of this specific technology (manufacture of 4-hydroxybutyraldehyde) is the problem of separating the rhodium catalyst from the aqueous extract of 4-hydroxybutyraldehyde. In practice, the aqueous extract is limited to about 10 percent 4-hydroxybutyraldehyde to suppress the loss of rhodium to the aqueous phase as is noted in U.S. Pat. No. 4,567,305 wherein the catalyst system consisted of rhodium and triphenylphosphine. U.S. Pat. No. 4,678,857 discloses that 5 mg of rhodium per liter of aqueous phase was extracted into the aqueous phase when the 4-hydroxybutyraldehyde concentration was 38 percent by weight.

A problem inherent in the described extraction procedure is the separation of the rhodium-containing, organic phase from the 4-hydroxy-butyraldehyde-containing aqueous extract. U.S. Pat. No. 4,678,857 proposes that this problem may be overcome by the use of halogenated aromatic compounds to increase the density differences between the organic layer and the aqueous layer. Brominated aromatic compounds are, in general, undesirable from the standpoint of toxicity and as potential catalyst poisons. The use of the aqueous extracts of 4-hydroxybutyr-aldehyde as feedstocks for catalytic hydrogenation to 1,4-butanediol is disclosed in U.S. Pat. Nos. 4,083,882 and 4,064,145. Once again, the relatively low concentration of 4-hydroxybutyraldehyde in the aqueous solution used in the hydrogenation requires a large amount of energy to remove the water from the dilute 1,4-butanediol product.

U.S. Pat. No. 5,138,101 discloses the separation of high-boiling aldehydes from hydroformylation solutions comprising a high-boiling aldehyde, catalyst components comprising rhodium and an organophos-phine compound, and a hydroformylation solvent by intimately contacting (extracting) the mixture with a solution comprising a primary alkanol such as methanol and water. The extraction mixture comprising the hydro-formylation and alkanol/water solutions is allowed to separate into 2 phases: a hydroformylation solvent phase containing the catalyst components and an alkanol/water phase containing the aldehyde. The hydroformylation solvent phase may be returned to the hydroformylation reactor and the aldehyde-containing alkanol/water phase may be processed further, either to recover the aldehyde or to convert the aldehyde to other compounds. An alkanol, particularly methanol, is an essential feature of the process described in U.S. Pat. No. 5,138,101

U.S. Pat. No. 4,376,208 discloses the hydroformylation of 2,5-dihydrofuran employing a catalyst system comprising a rhodium-triarylphosphine complex in the presence of a tertiary amine cocatalyst. A. Polo, et al., *Organometallics*, 11, 3525 (1992), also disclose the hydro-formylation of dihydrofurans and teach that the most effective catalysts are rhodium catalysts promoted with trialkyl phosphites. In each of these cases, the catalyst system caused the yield of the 3-FTHF to depend critically upon the reaction conditions. One reason for this is that an integral component of the catalyst system was a basic amine, which, in addition to the hydroformylation, promoted the aldol condensation of the formyl-reaction product. Therefore, even under conditions in which the initial yields of the 3-FTHF may be high, the isolated yields are not.

FTHF's, especially the 3-isomer, are valuable intermediates useful in the manufacture of commercial compounds. FTHF's may be produced by contacting 2,5-DHF with synthesis gas comprising carbon monoxide and hydrogen in the presence of a rhodium-phosphorus catalyst system and a hydroformylation solvent according to known hydroformylation procedures. Such hydroformylation of 2,5-DHF typically produces 2-FTHF and 3-FTHF in molar ratios of about 0.001:1 to 3.5:1.

Recovery of the 3-FTHF product presents technical difficulties such as the formation of hemiacetal oligomers, acetal oligomers, and aldol condensation compounds from the hydroformylation products. The formation of these by-products is catalyzed by basic materials such as the phosphine and the phosphite components of the hydroformylation catalyst, or even spontaneously, especially during distillation at high temperatures. Recycling the catalyst system after removing the products by distillation or gas sparging is beset with the problem of removing these high-boiling by-products without damaging the catalyst. Usually, the high-boiling by-products continue to accumulate until the catalyst becomes blocked and loses activity. At that point, the only alternative is to discard the inactivated catalyst and start with a fresh catalyst charge. The formation and accumulation of the high-boiling by-products, aided by the base-catalyzed condensations, renders distillation an impractical method of recovering 3-FTHF from hydroformylation product solutions.

The usual formation of high boiling by-products during the hydroformylation reaction typically amounts to less than 2 percent of the total product as a result of the low reaction temperature. The high boiling points and dielectric constants of the FTHF's render a gas sparging recovery impractical at the 2 megaPascal reaction pressure. Vacuum distillation at a base pot temperature of up to 130° C. recovers only 40 to 70 percent of the FTHF's present. Oligomeric by-products, formed at the distillation base pot temperatures, account for the remainder of the material balance. The bulk of these oligomers are hemiacetals which, upon heating, release the free monomer via a heat-promoted deoligomerization. For example, by heating the base pot temperature to 185° C., the total FTHF recovery will increase to as much as 80 to 96 percent of the total produced. However, many rhodium/phosphine catalyst systems are sensitive to high reaction temperatures as is disclosed in U.S. Pat. No. 4,277,627 and other literature. Beyond 130° C., the hydroformylation catalyst begins to decompose with the phosphine undergoing a rhodium-promoted loss of side groups and the rhodium metal itself eventually plating out.

I have discovered that an equilibrium mixture of FTHF's and the hydrates thereof, i.e., DHMTHF's, may be separated from hydroformylation solutions comprising FTHF's, catalyst components comprising rhodium and an organophosphorus compound, and a hydroformylation solvent by intimately contacting (extracting) the mixture with water which is essentially devoid of an alkanol. The extraction mixture comprising the hydroformylation and water solutions is allowed to separate into 2 phases: a hydroformylation solvent phase containing the catalyst components and a water phase containing 2- and 3-FTHF's and 2- and 3-DHMTHF's. The hydroformylation solvent phase may be returned to the hydroformylation reactor without further treatment and the water phase containing the FTHF's and their hydrates may be processed further, either to recover the aldehydes or to convert the aldehydes into other compounds. Any FTHF which is not extracted during one cycle returns to the hydroformylation reactor along with the hydroformylation solvent and may be recovered in a subsequent extraction. Most of what little oligomeric material that is produced during hydroformylation also is extracted into the aqueous phase, thereby purifying the catalyst solution and extending the number of hydroformylation cycles before a catalyst replacement is necessary. For example, during pilot studies the oligomeric high-boiler content remaining in the recycled catalyst solution after 19 extractions, recoveries, and recycles to the hydroformylation reactor remained below 0.5 percent.

Comparing distillation and extraction recovery methods, the best that distillation can do is an 80 to 96 percent recovery of the FTHF's as compared to 99+ percent recovery through extraction. The number of recycles of catalyst before replacement is necessary typically is about 1 to 12 with distillative recovery whereas at least 60 or more recycles are possible through the use of the extraction procedure described herein. The decline in catalyst activity prior to the catalyst replacement is several percent per recycle depending on the severity of the distillation conditions versus no loss through extraction. The only losses during extraction of either the product or the catalyst are physical losses caused by incomplete separation of the phases and by discarded slip-streams.

The process of the present invention therefore provides a means for producing an aqueous solution, essentially devoid of alkanol, containing a mixture of compounds having the formulas:

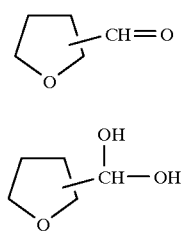

which comprises (1) intimately contacting a hydroformylation product solution comprising (i) 20 to 80 weight percent of an aldehyde of formula (I); (ii) hydroformylation catalyst components comprising rhodium and an organophosphorus compound, and (iii) 80 to 20 weight percent of a an organic hydroformylation solvent, with water essentially devoid of alkanol; (2) allowing the mixture of step (1) to separate into 2-phase mixture; and (3) separating the 2-phase mixture to obtain (a) a hydroformylation solvent phase containing catalyst components and (b) a water phase containing the compounds of formulas (I) and (II); wherein the volume ratio of water to hydroformylation product solution employed in step (1) is about 0.1:1 to 4:1; the hydroformylation product solution employed in step (1) contains less than about 15 weight percent of 2,5-DHF, 2,3-DHF, tetrahydrofuran (THF), or a mixture of any 2 or more thereof; and the mole ratio of compound (I) to compound (II) is about 0.05:1 to 20:1.

The concentration of compound (II) present depends on the concentration of the aldehyde in the aqueous solution. For example, when the concentration of aldehyde (I) and diol (II) is about 90%, the diol constitutes about 65% of the total of compounds (I) and (II) and when the concentration of aldehyde (I) and diol (II) is about 50%, the diol constitutes about 80% of the total of compounds (I) and (II), and when the concentration of aldehyde (I) and diol (II) is about 10%, the diol constitutes about 98% of the total of compounds (I) and (II). In fact, the high percentage of compound (II) at all except the very lowest water concentrations emphasizes how tenaciously the FTHF's hold onto water. Not surprisingly, when water is scarce, aldehyde (I) reacts with diol (II) forming the hemiacetal of aldehyde (I). However, the hemiacetal concentration typically is less than about 2%, usually not more than 0.5%, of the total FTHF present when the concentration of aldehyde (I) and diol (II) is about 60%. The process may be operated in a manner whereby essentially none of the catalyst system components, e.g., a catalytically-active, complex rhodium-phosphorus compound and additional or excess phosphine or phosphite, is extracted by the water solution. Thus, operation of the recovery process does not result in any significant loss of catalyst from the hydroformylation production system since the hydroformylation solvent phase containing the catalyst components may be recycled to the hydroformylation reactor. The water phase may be used as the feed to other processes wherein the compounds of formulas (I) and (II) are converted to other compounds such as alkanols by hydrogenation. Alternatively, the aldehyde may be isolated by the removal of the water by distillation under reduced pressure although the recovery of the purified, dry aldehyde (I) is not very efficient for the reasons discussed below.

The formation of the diols (II) under abundant water conditions and of hemiacetals under low water conditions is based on a strong tendency of the aldehydes (I) to react with hydroxyl-containing materials in general. But the product of the reaction between the aldehydes (I) and a hydroxyl-containing material is itself a hydroxyl-containing material, albeit with a higher molecular weight. So at very low water content, hemiacetal oligomers of ever increasing molecular weight are formed incorporating ever increasing percentages of the free aldehydes (I) into the growing oligomer.

The consequences of this ever increasing molecular weight of the hemiacetal oligomers are manifold. First, the temperature in the distillation pot rises. At these higher temperatures, the formation of the hemiacetal oligomers eventually reverses releasing the free aldehydes (I) and eventually the water also. But the rising temperature also allows impurities to catalyze the irreversible conversion of the hemiacetal oligomers, free aldehydes (I), and the diols (II) into other materials such as acetal oligomers by the release of water, aldol condensation products, and Tischenko esters. To the extent that these irreversible byproducts are formed, the recovery of pure free aldehydes (1) is lowered. The extent of this loss depends on the extent of the impurities in the original product, but can vary from 2 percent to as much as 70 percent under typical impurity level conditions.

Since the formation of the hemiacetal oligomers is reversible releasing the free aldehydes (I) and water, a second consequence of the tendency to form higher molecular weight oligomers is that the distilled product never becomes scrupulously dry. Most of the water released by this de-oligomerization flashes through the distillate into the vacuum traps owing to a 50° C. or more difference in boiling points between water and the free aldehydes (I). Nevertheless, water levels below 200 PPM are difficult to attain because of the strong tenacity the aldehydes (I) have to hold water.

Another related consequence is the problem in separating 2-FHTF from 3-FTHF despite their 25° C. difference in boiling points at 25 mm Hg pressure. This separation is facile until the deoligomerization of the hemiacetal begins to release 2-FHTF, the lower boiling isomer. While forming, the hemiacetal oligomers incorporate 2-FTHF and 3-FTHF free aldehydes (I) at random. Therefore, while thermally decomposing, they also release 2-FTHF and 3-FTHF free aldehydes (I) at random. So, the distilling 3-FTHF, previously freed of the lower boiling 2-FTHF by the fractionation process, again becomes contaminated with 2-FTHF. I have found this separation possible by keeping the disitllation base pot temperature below about 110° C. Up to this temperature, the deoligomerization of the hemiacetal oligomer is not significant so that the release of the 2-FTHF contaminant is also not significant. However, at this point 30 to 70 percent of the total free aldehydes (I) and diols (II) remain bonded in oligomeric materials. The only alternative to recovering the 2-FTHF and the 3-FTHF for subsequent separation at this point is to collect the combined free aldehydes (I) released by the deoligomerization for subsequent refractionation. I have found that the free aldehydes (I) collected from the deoligomerization at base distillation pot temperatures of about 110° C. to about 185° C. suitable for this reprocessing. An additional small amount of material may be collected from base distillation pot temperatures of about 185° C. to about 230° C.; however, its color becomes increasingly darker yellow and its free aldehyde (I) and diol (II) content becomes increasingly lower as the base pot temperature rises. The material remaining in the base pot following this secondary 2-FTHF and 3-FTHF recovery represents about 2 percent to about 30 percent of the amount of free aldehydes (I) and diols (II) originally fed.

The final consequence of the increasing molecular weight of the oligomers is that avoiding water does not prevent their formation. The affinity of the free aldehydes (I) for hydroxyl-containing materials is caused by an electron deficiency which any electron pair donor can satisfy. In the absence of other electron pair donors, the electron pairs of the free aldehyde (I) carbonyl group suffice leading irreversibly to polyacetals. So distillation of anhydrous free aldehydes (I) does not prevent the formation of oligomers. On the contrary, it increases the loss of free aldehydes (I) by increasing the formation of irreversible oligomers in contrast to the hydroxyl-containing materials, which form greater amounts of reversible oligomers.

Stated in alternative wording, water removal by fractional distillation at reduced pressure occurs readily until the water content falls below about 10 weight percent. At this point the distillation pot mixture consists mainly of the free aldehyde [FTHF, compound (I)] and the gem glycol [DHMTHF, compound (II)]. Any free water which exists is primarily water which is released from compound (II) by the equilibrium shifting to make water and compound (I). However, as the amount of compound (I) increases, it competes in compound (II) for the hydroxyl groups with the shifting equilibrium, which releases water. When compound (I) does react with compound (II), it forms compound (III) with n equal to 2, a hemiacetal, which is also a two-unit oligomer of FTHF.

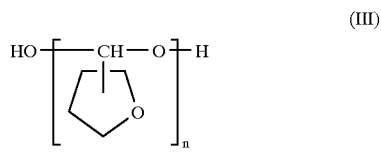

(III)

When in the hemiacetal form with n equal to or greater than 2, compound (III) will not release water. Even though it is still in equilibrium with the other components in the system, it must first decompose step by step into n-1 units of compound (I) and one unit of compound (II) before compound (II) can, in turn, decompose into one more unit of compound (I) and water. Since compound (III) is itself a diol, it could also add more existing free compound (I) to form another compound (III) with n increased by 1. In fact, when the concentration of free hydrophilic compound (I) climbs high enough with an insufficient amount of water OH groups to react with, this is exactly what happens. The effect is twofold: first, the FTHF effectively holds onto the water more tenaciously as the water removal progresses, and second, the average molecular weight of the hemiacetals increases at the same time.

All existing compound's (III) in the distillation base pot eventually contain a sizable amount of the free aldehyde originally fed. Incorporation of the formyltetrahydrofurans into the compound's (III) is random consisting of 2-formyltetrahydrofuran and 3-formyltetrahydrofuran in proportion to what existed originally in the bulk solution. The breakdown of compound's (III), however, is not random with the larger hemiacetal oligomers tending to require higher temperatures to decompose back into the monomeric compound (I) and water. This constitutes the primary problem in separating both of the last traces of water and the free FTHF isomers.

With a 23° C. difference in boiling points (2-FTHF boiling point, 39–42° C./14 mm, and 3-FTHF boiling point, 62–64° C./14 mm), the two isomers should be readily separated with only a few theoretical plate distillation column. However, when nearly all free lower-boiling 2-FTHF has been removed and the higher-boiling free 3-FTHF starts distilling, the base pot temperature also rises. This temperature rise causes progressively more of the random compound's (III) to deoligomerize. With the newly liberated water and 2-FTHF in the distillation pot at temperatures substantially above their boiling points, they flash into the product thereby contaminating it and making quantitative separation of the isomers and dehydration very difficult.

As mentioned hereinabove, the hydroformylation product solution employed in the present invention comprises, in addition to at least one of the above-described aldehydes, a catalyst system comprising rhodium and an organophosphine compound, and a hydroformylation solvent. The rhodium component of the catalyst system can be provided by any one of various rhodium compounds soluble in the organic reaction medium in which the hydroformylation is carried out. Examples of such soluble rhodium compounds include tris(triphenylphosphine)rhodium chloride, tris (triphenylphosphine)rhodium bromide, tris (triphenylphosphine)rhodium iodide, tris (triphenylphosphine)rhodium fluoride, rhodium 2-ethylhexanoate dimer, rhodium acetate dimer, rhodium propionate dimer, rhodium butyrate dimer, rhodium valerate dimers, rhodium carbonate, rhodium octanoate dimer, dodecacarbonyltetrarhodium, rhodium(III) 2,4-pentanedionate, rhodium(l) dicarbonyl acetonylacetonate, tris(triphenylphosphine)rhodium carbonyl hydride [(Ph3P:)3Rh(CO)—H], and cationic rhodium complexes such as rhodium(cyclooctadiene)bis(tribenzylphosphine) tetraflouroborate and rhodium (norbornadiene)bis (triphenylphosphine) hexaflourophosphate.

The activity and selectivity of the catalyst system usually is relatively insensitive to the source of the rhodium. The concentration of rhodium [Rh] in the catalyst solution may be in the range of about 0.1 to 100,000 ppm although very low concentrations of rhodium are not commercially desirable since reaction rates will be unacceptably low. The upper limit on the rhodium concentration is not critical and is dictated principally by the high cost of rhodium. Thus, the concentration of rhodium [Rh] in the catalyst solution preferably is in the range of 10 to 10,000 and, most preferably, 100 to 5000 ppm.

Examples of the organophosphine or phosphite component of the catalyst system are described in the patents referred to herein, including the references cited therein. Additional organophosphines are disclosed in U.S. Pat. Nos. 4,742,178, 4,755,624, 4,774,362, 4,871,878, 4,873,213 and 4,960,949. Tertiary (trisubstituted) phosphine and phosphite compounds may be employed as the organophosphorus component of the catalyst system. Examples of such phosphines and phosphites include tributyl-phosphine, tributylphosphite, butyidiphenylphosphine, butyidiphenylphos-phite, dibutylphenylphosphite, tribenzylphosphine, tribenzylphosphite, tricyclohexylphosphine, tricyclohexylphosphite, 1,2-bis (diphenylphosphino)-ethane, 1,3-bis(diphenylphosphino) propane, 1,4-butanebis(dibenzylphos-phite), 2,2'-bis (diphenylphosphinomethyl)-1,1'-biphenyl, and 1,2-bis (diphenylphosphinomethyl)benzene. Typical phosphine and phosphite ligands may be represented by the general formulas

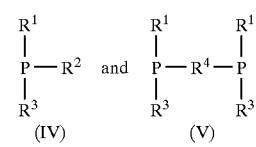

-continued

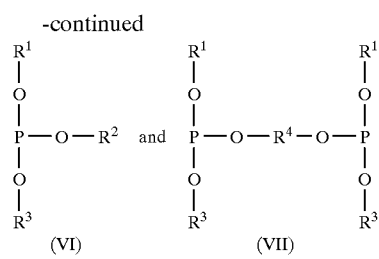

wherein $R^1$, $R^2$ and $R^3$ are the same or different and each is hydrocarbyl containing up to about 12 carbon atoms and $R^4$ is a divalent hydrocarb-ylene group which links the 2 phosphorus atoms through a chain of 2 to 8 carbon atoms. Examples of the hydrocarbyl groups which $R^1$, $R^2$ and $R^3$ may represent include alkyl including aryl-substituted alkyl such as benzyl, cycloalkyl such as cyclohexyl and cyclopentyl, and aryl such as phenyl and phenyl substituted with one or more alkyl groups. Alkylene such as ethylene, trimethylene and hexamethylene, cycloalkylene such as cyclohexylene, and phenylene, naphthylene and biphenylene are examples of the hydrocarbylene groups which $R^4$ may represent.

The organophosphorus component of the catalyst system preferably is a trisubstituted mono-phosphine compound such as those having formula (I) above. Triphenylphosphine, tricyclohexylphosphine, and, tribenzylphosphine are the most preferred organophosphorus compounds. The ratio of moles of organophosphorus compound to gram atoms of rhodium present in the catalyst system typically is about 2:1 to 10,000:1 with ratios in the range of 2.5:1 to 1000:1 being preferred and 3:1 to 100:1 being most preferred.

The solvent component of the hydroformylation product solution may be selected from various alkanes, cycloalkanes, alkenes, cycloalkenes and carbocyclic aromatic compound which are liquids at standard temperature and pressure and have a density which is at least 0.02 g/mL different from the density of the water extraction solvent employed. The formyltetrahydrofurans solubility in several of the aliphatic and cycloaliphatic solvents is limited, but this fact causes no problem during the hydroformylation reaction and subsequent extraction provided sufficient agitation is provided to keep the two reaction phases entering the extractor at similar rates. Likewise, several of the alkenes and cycloalkenes can themselves undergo the hydroformylation reaction, but this fact also causes no problem provided the olefin substitution is sufficient to keep its hydroformylation small relative to the hydroformylation of the 2,5-dihydrofuran. Specific examples of such solvents include alkane and cycloalkanes such as dodecane, decalin, octane, iso-octane mixtures, cyclohexane, cyclooctane, cyclododecane, methylcyclohexane; aromatic hydrocarbons such as benzene, toluene, ethylbenzene, xylene isomers, tetralin, cumene, alkyl-substituted aromatic compounds such as the isomers of diisopropylbenzene, triisopropylbenzene and tert-butylbenzene; and alkenes and cycloalkenes such as 1,7-octadiene, dicyclopentadiene, 1,5-cyclooctadiene, octene-1, octene-2, 4-vinylcyclohexene, cyclohexene, 1,5,9-cyclododecatriene, pentene-1 and crude hydrocarbon mixtures such as naphtha and kerosene.

Generally, solvents having polar functional groups, e.g., ketones and esters, or atoms other than carbon and hydrogen are not preferred because such solvents possess too much water solubility and/or tendency to form emulsions to give satisfactory partitioning characteristics and/or adversely affect the catalyst system. However, higher molecular weight polar ketone, ether, and ester polar compounds, such as isobutyl isobutyrate and bis(2-ethylhexyl) phthalate, have been found to give good results. The preferred hydroformylation solvents have a density in the range of about 0.6 to 0.9 and are selected from esters having about 6 to 20 carbon atoms, alkanes having about 5 to 20 carbon atoms, alkyl-substituted benzenes having about 7 to 15 carbon atoms, tetrahydro-naphthalene, and decahydronaphthalene.

The concentration of the FTHF's in the hydroformylation product solution is not critical with wide ranges giving acceptable results. For example, the concentration of the FTHF's in the hydroformylation product solution may be in the range of about 20 to 80 weight percent, preferably about 50 to 70 weight percent, based on the total weight of the hydroformylation product solution. Similarly, the concentration of the hydroformylation solvent in the hydroformylation product solution can be varied widely. The practical upper limit depends on the limit of solvent relative to product one wishes to circulate with there being no particular advantage or disadvantage in circulating large volumes. At 3 or 4 solvent volumes per product volume, the preferred upper limit is about 80 volume percent solvent. The practical lower limit depends on the density of the organic hydroformylation solvent and of the aqueous extractant with the proviso that the density of the total organic phase should be at least 0.02 g/mL less than the density of the hydroformylation product solution so that the hydroformylation solvent phase will separate from and rise through the countercurrent aqueous phase. For example, with toluene (d=0.8669) as the solvent and pure water (d=1) as the aqueous extractant, the practical lower preferred range is about 35 volume percent solvent. The hydroformylation solvent preferably constitutes about 40 to 70 weight percent, most preferably about 35 to 50 weight percent, of the total volume of the hydroformylation product solution. The rhodium and organophosphorus catalyst components typically constitute less than about 10 weight percent of the hydroformylation product solution.

Another factor affecting the selection of the hydroformylation solvent is the solubility or partitioning of the solvent into the aqueous phase. If the solubility of the hydroformylation solvent in the aqueous phase is greater than the catalyst components, the catalyst concentration gradually will rise in the recycle catalyst and supplemental solvent additions will be necessary. If the solubility of the hydroformylation solvent in the aqueous phase is less than the catalyst components, the catalyst concentration will gradually fall in the recycle catalyst and supplemental catalyst additions will be necessary. Since both the catalyst system and the organic hydroformylation solvent exhibit some solublity in the aqueous phase, the addition of solvent and catalyst components to the recycle catalyst normally is necessary over prolonged operation of the hydroformylation/extraction process. The preferred supplement rate is usually about 1 to 5 volume percent of the total recycle catalyst volume per cycle unless an extraordinary amount of emulsion is formed in the countercurrent extractors or the solvent has an extraordinary solubility in the aqueous extractant.

In accordance with the first step of the extraction process of the present invention, the hydroformylation product solution described above is imtimately contacted with water. The weight ratio of water:hydroformylation product solution typically may vary from about 0.1:1 to 4:1. The actual ratio depends more on the FTHF content of the reaction mixture than on its total volume. Thus, a weight ratio of 3:1 to 1:3 of water to the FTHF content is preferred with a weight ratio of 2:1 to 1:2 being most preferred. Within the most preferred solvent concentrations of 45 to 60 volume percent, the most preferred ratio of water to the total reaction mixture becomes a weight ratio of 1.3:1 to 1:10.

The evidence for the formation of the diols (II) and oligomers (III) was shown with the following experiments: The FTHF's exhibit high water solubility due to a strong interaction with water seemingly beyond simple dielectric solvent interactions. Thus, temperature rises exceeding 15° C. during the water extraction of the crude hydroformylation product solution and aqueous product densities significantly higher than those of either pure water (d=1) or pure 3-formyltetrahydrofuranm (d=1.078) suggest the formation of one or more new, high-density materials during the extraction. The densities of aqueous solutions of 3-FTHF at 23° C. are shown in Table I wherein FTHF Conc is the weight percent concentration of 3-FTHF in essentailly pure water.

TABLE I

| FTHF Conc | Density |
|---|---|
| 0 | 1.00 |
| 10 | 1.020 |
| 20 | 1.044 |
| 30 | 1.064 |
| 40 | 1.086 |
| 50 | 1.109 |
| 60 | 1.131 |
| 70 | 1.147 |
| 80 | 1.156 |
| 90 | 1.140 |
| 100 | 1.078 |

The maximum density shown in Table I corresponds approximately to the composition for 3-DHMTHF. 3-DHMTHF contains the elements of one 3-FTHF molecule (MW=100.11831) and one $H_2O$ molecule (MW=18.01534). Thus, the weight percent equivalent of 3-FTHF in 3-DHMTHD then is 100.11831/(100.11831+18.01534)= 84.75 wt.% compared with a maximum in the weight percent 3-FTHF versus density chart at 80 weight percent. Confirmation of the formation of 3-DHMTHF when 3-FTHF is added to water comes from proton Nuclear Magnetic Resonance spectroscopy. At room temperature, 50 weight percent solutions of aqueous 3-FTHF show two components: 79 mole percent 3-DHMTHF and only 21 mole percent 3-FTHF. Furthermore, changing the water concentration either directly or by using water miscible solvents reversibly changes the 3-DHMTHF:3-FTHF mole ratio indicating a rapidly established equilibrium between the two components as well as showing their relative stability. The relative amounts of 3-FTHF and 3-DHMTHF at varying water/3-FTHF concentrations as determined by proton nuclear magnetic resonance spectroscopy are shown in Table II wherein the values given for "Water", "3-FTHF" and "Solvent" are weight percentages based on the total weight of the 3 component composition and "Solvent" refers to $CD_3COCD_3$(NMR solvent).

TABLE II

| Composition | | | Mole Percent | |
|---|---|---|---|---|
| Water | 3-FTHF | Solvent | 3-FTHF | 3-DHMTHF |
| 45.0 | 55.0 | 0.0 | 21.0 | 79.0 |
| 37.6 | 54.4 | 8.0 | 24.9 | 75.1 |
| 36.9 | 46.6 | 16.5 | 28.8 | 71.2 |
| 31.4 | 43.5 | 25.1 | 33.3 | 66.7 |
| 24.1 | 32.0 | 43.9 | 43.4 | 56.6 |
| 19.8 | 26.2 | 54.0 | 51.1 | 48.9 |
| 15.2 | 20.2 | 64.6 | 58.1 | 41.9 |
| 10.4 | 13.8 | 75.8 | 68.8 | 31.2 |
| 6.1 | 6.3 | 87.6 | 78.4 | 21.6 |

In Table II the value given for the 3-FTHF component is the amount of 3-FTHF dissolved in the composition although in aqueous solution it exists both as 3-FTHF and 3-DHMTHF. Some of the 3-FTHF in the water solution also exists in the form of an acetal, e.g., depending on the concentration, up to about 70 mole percent (at very high concentrations) but usually only about 0.5 mole percent (at 50 weight percent concentration) of the 3-FTHF is in the form of an acetal having the structure:

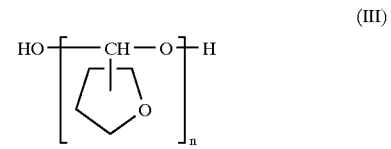

(III)

wherein n is 2.

Additional confirming evidence may be found in the linear dependence (see Table III below) of the extraction coefficient (K), defined below, on the concentration of water in the aqueous phase. Instead of remaining constant as required by a simple solvation equilibrium between two phases, $[3\text{-Formyltetrahydrofuran}]_{Solvent} \leftrightharpoons [3\text{-Formyltetrahydrofuran}]_{Aqueous}$ the linear dependence on the concentration of water suggests the following equilibrium:

$3\text{-Formyltetrahdyrofuran} + H_2O \leftrightharpoons 3\text{-Dihydroxymethyltetrahydrofuran}$ in which the solubility of the two equilibriating components is different between the two phases.

I have found that the extraction of both the catalyst and the FTHF's is best represented by their partition coefficient. For example, the partition coefficient as defined below for FTHF partitioning between an aqueous and toluene phase is 5.9 at room temperature at a 50 weight percent water concentration (31 Molar) in the aqueous phase.

$$K_{3FTHF} = 5.9 = \frac{[3\text{-FTHF}]_{Aqueous}}{[3\text{-FTHF}]_{Toluene}}$$

In this case, $K_{3FTHF}$ is the partition coefficient for 3-FTHF, $[3\text{-FTHF}]_{Aqueous}$ is the concentration of 3-FTHF in the aqueous phase, and $[3\text{-FTHF}]_{Toluene}$ is the concentration of 3-FTHF in the toluene phase. The linear dependence of the partition coefficient on the concentration of extracting water may be seen in Table III in which M is the molarity of water, K(toluene) is the partition coefficient between water and the solvent toluene, and K(3fthf) is the partition coefficient between water and the substrate 3-FTHF.

TABLE III

Dependence of Partition Coefficients (K) on the Concentration of Water in the Aqueous Phase During Water Extractions of 3-FTHF/Toluene Solutions

| [H2O](AQ) | | | |
|---|---|---|---|
| M | Wt. % | K(3fthf) | K(toluene) |
| 48.91218 | 86.1348 | 9.118963 | 0.010161 |
| 48.23674 | 84.72044 | 8.997923 | 0.010402 |
| 47.39479 | 82.96888 | 8.847047 | 0.010717 |
| 46.31643 | 80.74376 | 8.653805 | 0.011141 |
| 44.88637 | 77.82406 | 8.397537 | 0.011746 |
| 42.9 | 73.8262 | 8.041581 | 0.012676 |
| 39.95486 | 68.01833 | 7.513811 | 0.014284 |
| 35.11341 | 58.77008 | 6.646223 | 0.017725 |
| 42.77033 | 73.55831 | 8.018344 | 0.012741 |
| 41.42245 | 70.88316 | 7.776803 | 0.013445 |
| 39.74471 | 67.5938 | 7.476152 | 0.014411 |

TABLE III-continued

Dependence of Partition Coefficients (K) on the Concentration of Water in the Aqueous Phase During Water Extractions of 3-FTHF/Toluene Solutions

| [H2O](AQ) | | | |
|---|---|---|---|
| M | Wt. % | K(3fthf) | K(toluene) |
| 37.60019 | 63.45289 | 7.091853 | 0.015812 |
| 34.76379 | 58.0822 | 6.583571 | 0.018022 |
| 30.83304 | 50.83107 | 5.879181 | 0.021992 |
| 24.95611 | 40.38408 | 4.826035 | 0.031122 |
| 36.61842 | 61.57454 | 6.915922 | 0.016527 |
| 34.60081 | 57.76969 | 6.554365 | 0.018164 |
| 32.09317 | 53.12207 | 6.104996 | 0.020581 |
| 28.89352 | 47.31806 | 5.531618 | 0.02448 |
| 24.66307 | 39.85205 | 4.773521 | 0.031727 |
| 18.70812 | 29.72398 | 3.706395 | 0.049514 |
| 30.45174 | 50.12216 | 5.810853 | 0.022449 |
| 27.76655 | 45.29974 | 5.329666 | 0.026136 |
| 24.43385 | 39.4445 | 4.732446 | 0.032213 |
| 20.18008 | 32.17144 | 3.970171 | 0.043874 |
| 14.44315 | 22.70328 | 2.942112 | 0.074328 |
| 24.26191 | 39.14077 | 4.701635 | 0.032585 |
| 20.90983 | 33.39555 | 4.100942 | 0.041442 |
| 16.74899 | 26.4487 | 3.355318 | 0.058986 |
| 11.32277 | 17.68473 | 2.38294 | 0.107693 |
| 18.03245 | 28.56244 | 3.585315 | 0.052493 |
| 14.00933 | 21.96798 | 2.864371 | 0.077913 |
| 8.925103 | 13.88343 | 1.953279 | 0.152787 |
| 8.925103 | 13.88343 | 1.953279 | 0.152787 |
| 11.73126 | 18.29434 | 2.456142 | 0.102111 |
| 7.037774 | 10.90603 | 1.615069 | 0.213472 |

Three extraction cycle equivalents are sufficient to recover the FTHF's essentially quantitatively from the hydroformylation solvent phase. The formation of emulsions during the extraction may result in lower extraction efficiencies although the unrecovered FTHF's merely recycle with the recycle catalyst back to the hydroformylation reactor where they remain unchanged and may be recovered during a subsequent aqueous extraction. Since such emulsions can require from about 2 to 48 hours or longer to completely separate, they should be avoided when possible, even when a coalescer is used to aid in their separation. The process of the present invention preferably uses a countercurrent extractor which minimizes turbulence (which causes the formation of emulsions) and acts as a coalescer so that the emulsion formation remains small.

The effect of emulsion formation on FTHF extraction is minimal for two reasons. First, the extraction moves the FTHF's from the organic phase into the aqueous phase where the countercurrent extractor can re-extract the aqueous phase and its emulsion several times. Thus, even a partition coefficient of 1 is sufficient to remove 88 percent of the product with a three cycle extraction equivalent. Secondly, even a 10 percent emulsion (a large number) will only lower a 5.9 partition coefficient to 4.8. In this case, the three cycle extraction equivalent is still sufficient to recover over 99 percent of the FTHF's entering the extractor.

Because of the FTHF's and DHMTHF's act as secondary extraction solvents, some, e.g., up to about 2 weight percent, of the rhodium and organophosphorus components of the hydroformylation catalyst system may be extracted into the aqueous extraction phase. The amounts of the catalyst components extracted into the aqueous phase usually are significantly greater when a large amount of emulsion is formed regardless of any favorable value for its partition coefficient. In that case, the partition coefficient between the aqueous and the toluene phases as defined below is 0.0043 at room temperature with 50 weight percent water $$K_{Phosphine} = 0.0043 = \frac{[Phosphine]_{Aqueous}}{[Phosphine]_{Toluene}}$$

in the aqueous phase. In this case, $K_{phosphine}$ is the partition coefficient for triphenylphosphine, $[Phosphine]_{Aqueous}$ is the concentration of triphenylphosphine in the aqueous phase, and $[Phosphine]_{Toluene}$ is the concentration of triphenylphosphine in the toluene phase. Also in this case the partition coefficient shows a water dependence, but only because 3-FTHF and 3-DHMTHF (with their water dependent concentrations) act as secondary extraction solvents. Rhodium, the other component of the catalyst, exists primarily as rhodium (I) hydrido carbonyl bis (triphenylphosphine) complex and accompanies the triphenylphosphine with a similar partition coefficient. Three cycle equivalent extractions leaves 98.7 percent of the triphenylphosphine and rhodium in the toluene phase. But the 10 percent emulsion changes the effective partition coefficient to 0.095 so that the triphenylphosphine and rhodium remaining in the toluene phase is now only 76 percent of the amount fed.

Catalyst losses of this magnitude as well as the accompanying downstream product contamination are not acceptable. In both cases, but especially in the latter, it may be advantageous or even necessary to subject the aqueous extraction phase to a second extraction wherein the aqueous phase obtained from the process described hereinabove is intimately contacted with substantially uncontaminated hydroformylation solvent. The second extraction not only recovers in the organic solvent any catalyst components, i.e., rhodium and/or organophosphorus compound, which are extracted into the water phase in the first or primary extraction but removes from the water phase catalyst materials which have a detrimental effect upon the distillation of the water phase to improve the purity of the desired 3-isomer. Preferably, the secondary extraction is carried out using a countercurrent extraction of the organic hydroformylation solvent and the aqueous extraction phase, using at least 0.05 volume of organic solvent per volume of the water phase. A more preferred volume ratio of the organic solvent to the water phase typically is in the range of about 0.1:1 to 0.5:1. The secondary extraction may be carried out at a temperature of about 0 to 70° C. with a range of about 15 to 35° C. being preferred. The organic solvent containing the catalyst components as well as the back-extracted FTHF's then may be recycled to the hydroformylation reactor to recover the recovered catalyst components and FTHF's from this extraction. However, to prevent excess dilution of the hydroformylation catalyst solution with the additional solvent, most of the additional solvent utilized in the secondary extraction normally first should be first recovered for reuse in the secondary extraction.

In this example, such a back extraction of the aqueous phase with fresh toluene is warranted. During the back extraction even if the emulsion percentage rises to 20 percent (an unlikely event), a three cycle equivalent extraction is sufficient to recover all but 0.3 percent of the phosphine and rhodium originally fed. Almost all other cases are better than this one. And with the high cost of the catalyst components, nearly quantitative recovery is important.

Because of the high water solubility of the FTHF's, no other additives are necessary to ensure their early complete extraction into an unmodified water extractant. The high polarity of the FTHF's and especially the DHMTHF's ensures the extraction of a minimum of the relatively non-polar hydroformylation solvent and catalyst components so their separation is also nearly complete. More specifically, addition of an alkanol and/or salt modifiers merely serves to increase the solubility of water in the recycle catalyst and of the hydroformylation solvent and catalyst components in the aqueous phase. More importantly, such modifiers represent contaminants which subsequently must be removed to obtain a substantially pure final product.

I also have found that the starting material, 2,5-dihydrofuran, and its isomer, 2,3-dihydrofuran, are excellent solubilizing agents (like tetrahydrofuran) for dissolving the relatively non-polar hydroformylation solvent into the aqueous extraction medium and, vice versa, water into the hydroformylation solvent. Thus, in the hydroformylation reactor, the solubilizing effect of 2,5-dihydrofuran, the starting material, on water into the organic hydroformylation solvent ensures a homogeneous reaction medium, which is important in avoiding reaction complications such as the hydrogenation of the starting material into tetrahydrofuran rather than its hydroformylation. Therefore, to minimize the necessity of recovering the catalyst components by back extraction with fresh solvent, it is important to avoid high concentrations of these tetrahydrofuran-like materials in the final, extractable product. This means conducting the hydroformylation at low temperatures to avoid isomerizing 2,5-dihydrofuran into 2,3-dihydrofuran; using synthesis gas without a substantial excess of hydrogen beyond the required 1:1 stoichiometry to avoid producing excessive amounts of tetrahydrofuran; and, conducting the reaction to high conversions to avoid significant amounts of 2,5-dihydrofuran in the hydroformylation product solution. Alternatively, these compounds may be removed by low temperature gas stripping or distillation prior to the extraction. As long as these three components remain below 50 percent of all furan derivatives in the product, the extraction will work (i.e. it will separate into two phases) albeit with considerable cross contamination of both extraction phases at the higher end of this range. A more desirable concentration keeps these three tetrahydrofuran-like components below 35 percent of all furan derivatives in the product. However, the hydroformylation product solution subjected to the extraction in accordance with the present invention contains less than about 15 weight percent, preferably less than about 10 weight percent, of 2,5-DHF, 2,3-DHF, THF or a mixture of any 2 or more thereof.

I have found that the solubility of the FTHF's in the water extractant is higher at lower extraction temperatures. Thus, no advantage is achieved by using temperatures greater than those of the hydroformylation reaction temperature, e.g., about 50 to 85° C., and superior results are obtained when the extraction temperature is lower than that of the hydroformylation reactor especially with exotherms up to 15° C. accompanying the solvation/reaction occurring during the aqueous extraction. The extraction process preferably is carried out at an initial temperature in the range of about 0 to 70° C. and most preferably in the range of about 25 to 45° C. The 25 to 45° C. range is the most practical from the standpoints of extraction efficiency, speed of reaching equilibration, and solvation/reaction exotherms.

The time over which the hydroformylation product solution and water are contacted, i.e., prior to phase separation, is dependent upon the speed at which the phases reach equilibrium. In practice this may vary from a minute or less to impractically long mixing times in excess of three hours.

In contrast to the published requirements for high conversions of allyl alcohol for successful aqueous product extraction during its hydroformylation into hydroxybutyraldehyde, I have found that a low 2,5-dihydrofuran conversion strategy referred to above not only is operable, but is preferred to produce a product containing very low levels of unwanted 2-FTHF. Due to the much higher boiling point and the presence of the hydroxyl group, this mode of operation is not suitable in the aqueous extractive product recovery following the hydroformylation of allyl alcohol. This mode of operation succeeds with 2,5-DHF since 2,5-DHF will hydroformylate only into 3-FTHF but it can also isomerize into 2,3-DHF which will hydroformylate into 2-FTHF, but at a much slower rate than the hydroformylation of 2,5-DHF. The separation of the unreacted DHF's from the reaction mixture prior to the aqueous extraction is simple because of their low boiling points. Thus, stopping the reaction at low 2,5-DHF conversions keeps the formation of 2-FTHF to a minimum by keeping the 2,3-DHF concentrations at low levels. Stripping the unreacted DHF's from the partially completed reaction allows their subsequent distillative separation with the removal of the unwanted 2,3-DHF and the return of the purified 2,5-DHF to the hydroformylation reactor. Using this operating technique while keeping the 2,5-DHF conversion below 50 percent lowers the 2-FTHF impurity content to 10 to 0.1 percent of its value at 95 percent 2,5-DHF conversion at a cost of less than 5 percent material removed as the 2,3-DHF. The resulting extracted aqueous product shows a ratio of 3-FTHF to 2-FTHF of about 200:1 to 20,000:1 at typical reaction conditions.

The hydroformylation of 2,5-DHF may be carried out at a temperature in the range of about 40 to 180° C. However, to minimize isomerization of the 2,5-DHF reactant to 2,3-dihydrofuran (2,3-DHF), the hydroformylation normally will be performed at a temperature in the range of about 50 to 85° C. Isomerization of the 2,5-DHF reactant to 2,3-DHF leads to the formation of a mixture of 2- and 3-FTHF. Coproduction of these isomers presents no problem in their extractive separation, but it does limit the upper yield of the desired 3-FTHF to about 30% because 2,3-DHF produces 2- and 3-FTHF in about a 3:1 ratio. The total pressure used in the hydroformylation may be in the range of about 0.01 to 35 mPa (about 1.5 to 5000 psig) with total pressures in the range of about 0.35 to 7 mPa (about 50 to 1000 psig) being preferred. The mole ratio of carbon monoxide to hydrogen in the synthesis gas may be about 3:1 to 0.3:1 with mole ratios of about 2:1 to 0.5:1 being more common. As mentioned hereinabove, the synthesis gas preferably does not contain a substantial excess of hydrogen to avoid producing excessive amounts of tetrahydrofuran The process of the present invention is further illustrated by the following examples. The following reference examples describe hydroformylation procedures for the production of the hydroformylation product solutions and formyltetrahydofurans which are employed in the process of the invention. As used herein, the percent conversion of a reactant is:

$$\frac{\text{Moles Reactant Converted}}{\text{Moles Reactant Fed}} \times 100$$

and the present percent selectivity to a particular compound:

$$\frac{\text{Moles Reactant Converted to Desired Product}}{\text{Moles Reactant Converted}} \times 100$$

REFERENCE EXAMPLE 1

To a 300 mL, stainless steel autoclave was charged 150 mL of 2,5-DHF (d=0.927,139 g, 1.93 moles), 37.6 mg of dicarbonyl rhodium (I) acetylacetonate (0.147 millimoles—mmol), and 95.4 mg of triphenylphosphine (0.364 mmol). The phosphorus to rhodium atomic ratio was 2.50 and the concentration of rhodium was 100 ppm (w/v). The autoclave was sealed and the run began by charging the system with 2.17 mPa (300 psig) of synthesis gas (hydrogen to carbon monoxide ratio=1.01:1) and rapidly stirring and heating the autoclave contents to 70° C. During the course of the reaction, the synthesis gas pressure was maintained at 2.17 mPa (300 psig) by periodic recharges of synthesis gas from a reservoir. Over 42 hours, the synthesis gas pressure drop amounted to a total of 45.95 mPa (6650 psig) and, at the end of this time, the uptake had nearly stopped.

Gas chromatographic (GC) analysis of a sample of the reaction product mixture showed a starting material conversion of 95.4%, a selectivity to 3-FTHF of 94.7% and a selectivity to 2-FTHF of 2.2%. Distillation of this product gave a material boiling at 83.5–85.5° C./32 Torr or 74.0–75.5° C./17 Torr which GC analysis showed was 98.9% pure 3-FTHF. During the course of this fractional distillation, the base temperature reached a maximum of 127° C. and the product recovery was only 54%. Gas chromatographic analysis of the distillation pot residue after completion of the distillation showed a multitude of oligomeric by-products caused, presumably, by the phosphine-aided aldol condensation of the aldehydes in the product.

This example demonstrates the results obtained when the hydroformylation product obtained from 25-DHF is recovered by distillation.

REFERENCE EXAMPLE 2

Reference Example 1 was repeated except the 2,5-DHF reactant was reduced to 75 mL and 75 mL of toluene solvent was added. The time required to achieve 95% conversion of the starting material as measured by GC analysis was 23.0 hours. The selectivities and ratio of 3-FTHF to 2-FTHF were essentially the same as in Example 1. The recovery of 99.0% pure 3-FTHF by distillation of the products of several of these combined experiments containing toluene solvent was 49%.

REFERENCE EXAMPLE 3

Reference Example 2 was repeated except the synthesis gas pressure was 4.58 mPa (650 psig). The time required to achieve 95% conversion of the starting material as measured by GC analysis was 23.5 hours. The selectivities and ratio of 3-FTHF to 2-FTHF were essentially the same as in Example 1.

REFERENCE EXAMPLE 4

Reference Example 2 was repeated except that the synthesis gas pressure was 0.79 mPa (100 psig). The time required to achieve 95% conversion of the starting material as measured by GC was 19.5 hours. The selectivities and ratio of 3-FTHF to 2-FTHF was essentially the same as in Example 1.

REFERENCE EXAMPLE 5

Reference Example 2 was repeated except that the amount of triphenylphosphine was increased to give a phosphorus-:rhodium atomic ratio of 12:1. The time required to achieve 95% conversion of the starting material was 18.0 hours. The selectivity to 3-FTHF was 91.9% and the selectivity to 2-FTHF was 7.9%.

REFERENCE EXAMPLE 6

Reference Example 5 was repeated except that the initial 2,5-DHF charge was 150 mL and the toluene solvent was omitted. The time required to achieve 95% conversion of the 2,5-DHF was 39.0 hours. The selectivity to 3-FTHF was 92.7% and the selectivity to 2-FTHF was 7.1%. This example demonstrates that the absence of an inert reaction solvent has no effect on the outcome of the hydroformylation reaction, even with significant changes in the phosphine component of the catalyst.

REFERENCE EXAMPLE 7

Reference Example 5 was repeated except the triphenylphosphine was replaced with tricyclohexylphosphine. The time required to achieve 95% conversion of the 2,5-DHF was 16.5 hours. GC analysis of the product at this point showed a 91.0% selectivity to 3-FTHF and a 8.2% selectivity to 2-FTHF.

REFERENCE EXAMPLE 8

Reference Example 5 was repeated except the triphenylphosphine catalyst component was replaced with an equimolar quantity of trimethylphosphite. The time required to achieve 95% conversion of the 2,5-DHF was 24.0 hours. GC analysis of the product showed an 89.2% selectivity to 3-FTHF and a 9.1% selectivity to 2-FTHF.

REFERENCE EXAMPLE 9

Reference Example 5 was repeated except the ratio of the hydrogen to the carbon monoxide in the synthesis gas was maintained at 2:1 rather than 1:1. The time required to achieve 95% conversion of the 2,5-DHF was 9.5 hours. GC of the product showed a 65.8% selectivity to 3-FTHF, a 25.0% selectivity to 2-FTHF, and a 9.0% selectivity to tetrahydrofuran. This example demonstrates the effect of changing the ratio of hydrogen to carbon monoxide in the synthesis gas on the outcome of the reaction.

REFERENCE EXAMPLE 10

Reference Example 5 was repeated except the rhodium source was changed to rhodium (II) 2-ethylhexanoate at a rhodium concentration of 100 ppm. The time required to achieve 95% conversion of the 2,5-DHF was 18.5 hours. The selectivity to 3-FTHF was 94.0% and the selectivity to 2-FTHF was 3.7%.

REFERENCE EXAMPLE 11

Reference Example 10 was repeated except that the rhodium concentration was 200 ppm and the amount of triphenylphosphine was increased to maintain a phosphorus to rhodium atomic ratio of 12:1. The time required to achieve 95% conversion of the 2,5-DHF starting material was 8.5 hours. The selectivity to 3-FTHF was 94.1% and the selectivity to 2-FTHF was 2.8%.

REFERENCE EXAMPLE 12

Reference Example 10 was repeated except that the rhodium concentration was 400 ppm and the amount of triphenylphosphine was increased to maintain a phosphorus to rhodium atomic ratio of 12:1. The time required to achieve 95% conversion of the 2,5-DHF reactant was 7.5 hours. The selectivity to 3-FTHF was 95.3% and the selectivity to 2-FTHF was 1.8%.

REFERENCE EXAMPLE 13

Reference Example 2 was repeated except the solvent was isooctane. The time required to achieve 95% conversion of the starting material as measured by GC analysis was 21.5 hours. The selectivities and ratio of 3-FTHF to 2-FTHF were essentially the same as in Example 1.

REFERENCE EXAMPLE 14

Reference Example 2 was repeated except the solvent was 1,3-diisopropylbenzene. The time required to achieve 95% conversion of the starting material as measured by GC analysis was 19.5 hours. The selectivities and ratio of 3-FTHF to 2-FTHF were essentially the same as in Example 1.

REFERENCE EXAMPLE 15

Reference Example 2 was repeated except the solvent was 2,2,4-trimethyl-1,3-pentanediol monoisobutyrate. The time required to achieve 95% conversion of the starting material as measured by GC analysis was 23.5 hours. The selectivities and ratio of 3-FTHF to 2-FTHF were essentially the same as in Example 1.

REFERENCE EXAMPLE 16

Reference Example 2 was repeated except the solvent was bis(2-ethylhexyl) phthalate. The time required to achieve 95% conversion of the starting material as measured by GC analysis was 21.5 hours. The selectivities and ratio of 3-FTHF to 2-FTHF were essentially the same as in Example 1.

EXAMPLES 1–36

The extraction examples were carried out under nitrogen in a separatory funnel using a calibrated, graduated cylinder to measure the volumes of the extracted phases and an uncorrected thermometer to measure the temperatures of the extraction. Final analyses were conducted after the initial exotherm had abated and all emulsions had completely separated. Each phase was analyzed by gas chromatography using a 20 M×0.25 mm DB 1701 capillary column at a flow rate of 3.5 cc/minute helium. Ethanol was the internal standard for the aliquot of the aqueous phase and n-dodecane was the internal standard for the aliquot of the catalyst phase. In each case, the temperature was checked so that the results agreed within 2° C.

The amounts of materials used in Examples 1–36 are shown in Table IV wherein the values given for 3-FTHF, Toluene and Water are the relative volume amounts of those materials used in each extraction example wherein the solution of 3-FTHF in Toluene was extracted with the relative amount of Water specified.

TABLE IV

| Example No. | 3-FTHF | Toluene | Water |
|---|---|---|---|
| 1 | 10 | 10 | 80 |
| 2 | 10 | 20 | 70 |
| 3 | 10 | 30 | 60 |
| 4 | 10 | 40 | 50 |
| 5 | 10 | 50 | 40 |
| 6 | 10 | 60 | 30 |
| 7 | 10 | 70 | 20 |
| 8 | 10 | 80 | 10 |
| 9 | 20 | 10 | 70 |
| 10 | 20 | 20 | 60 |
| 11 | 20 | 30 | 50 |
| 12 | 20 | 40 | 40 |
| 13 | 20 | 50 | 30 |
| 14 | 20 | 60 | 20 |
| 15 | 20 | 70 | 10 |
| 16 | 30 | 10 | 60 |
| 17 | 30 | 20 | 50 |
| 18 | 30 | 30 | 40 |
| 19 | 30 | 40 | 30 |
| 20 | 30 | 50 | 20 |
| 21 | 30 | 60 | 10 |
| 22 | 40 | 10 | 50 |
| 23 | 40 | 20 | 40 |
| 24 | 40 | 30 | 30 |
| 25 | 40 | 40 | 20 |
| 26 | 40 | 50 | 10 |
| 27 | 50 | 10 | 40 |
| 28 | 50 | 20 | 30 |
| 29 | 50 | 30 | 20 |
| 30 | 50 | 40 | 10 |
| 31 | 60 | 10 | 30 |
| 32 | 60 | 20 | 20 |
| 33 | 60 | 30 | 10 |
| 34 | 70 | 10 | 20 |
| 35 | 70 | 20 | 10 |
| 36 | 80 | 10 | 10 |

The results achieved in the extractions of Examples 1–36 are shown in Table V wherein the values given for Vol are the relative volumes of the Toluene and Aqueous Phases in each example, the values given for 3-FTHF, Toluene (To) and Water are the weight percentages of each component in the Toluene and Aqueous Phases (based on the total weight of each phase) and the values given for K are the partition coefficients for 3-FTHF calculated from:

$$K_{3\text{-FTHF}} = \frac{[3\text{-FTHF}]_{Aqueous}}{[3\text{-FTHF}]_{Toluene}}$$

wherein $K_{3\text{-}FTHF}$ is the partition coefficient for 3-FTHF, $[3\text{-FTHF}]_{Aqueous}$ is the concentration of 3-FTHF in the aqueous phase, and $[3\text{-FTHF}]_{Toluene}$ is the concentration of 3-FTHF in the toluene phase. The calculation of the partition coefficients was made at several different initial concentrations of the solvent, water, and 3-FTHF. To check the consistency of the results, several of these analyses were repeated and in all cases the repetitions agreed within 10 percent of one another. Where repeated, the analytical values given are averages of the plurality of analyses. The results of these experiments are summarized in Table V below. The purpose of these examples is to show the consistency of the partition coefficient calculations and the dependence of the partition coefficients on the water concentration.

TABLE V

| Example No. | Toluene Phase | | | | | Aqueous Phase | | | | | K |
|---|---|---|---|---|---|---|---|---|---|---|---|
| | Vol | 3FTHF | Tol | Water | Density | Vol | 3FTHF | Tol | Water | Density | |
| 1 | 9.4 | 1.4 | 98.4 | 0.2 | 0.8701 | 89.1 | 11.7 | 0.7 | 87.6 | 1.0240 | 9.7 |
| 2 | 18.6 | 1.8 | 98.0 | 0.2 | 0.8709 | 79.8 | 12.8 | 1.8 | 85.4 | 1.0264 | 8.2 |
| 3 | 29.6 | 1.8 | 98.0 | 0.2 | 0.8709 | 68.8 | 14.5 | 1.0 | 84.5 | 1.0302 | 9.5 |
| 4 | 39.6 | 2.2 | 97.7 | 0.1 | 0.8717 | 58.9 | 16.5 | 1.5 | 82.0 | 1.0343 | 9.1 |
| 5 | 50.6 | 3.1 | 96.8 | 0.1 | 0.8735 | 48.0 | 18.9 | 1.1 | 80.0 | 1.0396 | 7.4 |
| 6 | 61.6 | 3.9 | 95.9 | 0.2 | 0.8754 | 37.2 | 22.2 | 0.8 | 77.0 | 1.0468 | 6.8 |
| 7 | 71.8 | 4.3 | 95.0 | 0.2 | 0.8763 | 27.0 | 28.2 | 2.0 | 69.8 | 1.0595 | 7.8 |
| 8 | 83.2 | 5.0 | 94.8 | 0.2 | 0.8777 | 15.9 | 41.2 | 1.0 | 57.8 | 1.0878 | 10.2 |
| 9 | 8.1 | 3.5 | 96.3 | 0.2 | 0.8745 | 88.8 | 22.9 | 2.0 | 75.1 | 1.0482 | 7.8 |
| 10 | 19.9 | 4.0 | 95.9 | 0.1 | 0.8754 | 77.2 | 25.6 | 0.7 | 73.6 | 1.0541 | 7.8 |
| 11 | 29.8 | 4.0 | 95.9 | 0.1 | 0.8755 | 67.3 | 28.7 | 1.4 | 69.9 | 1.0608 | 8.7 |
| 12 | 41.1 | 5.5 | 94.3 | 0.2 | 0.8787 | 56.2 | 32.6 | 1.1 | 66.3 | 1.0691 | 7.2 |
| 13 | 51.8 | 5.5 | 94.3 | 0.2 | 0.8788 | 45.7 | 38.6 | 0.8 | 60.6 | 1.0820 | 8.6 |
| 14 | 64.5 | 9.3 | 90.6 | 0.1 | 0.8867 | 33.3 | 44.5 | 0.7 | 54.8 | 1.0949 | 5.9 |
| 15 | 76.2 | 11.1 | 88.7 | 0.2 | 0.8906 | 21.8 | 57.2 | 2.0 | 40.8 | 1.1222 | 6.5 |
| 16 | 9.4 | 6.3 | 93.6 | 0.1 | 0.8803 | 86.4 | 34.3 | 1.0 | 64.7 | 1.0729 | 6.7 |
| 17 | 20.4 | 6.5 | 93.3 | 0.2 | 0.8809 | 75.5 | 38.2 | 0.7 | 61.1 | 1.0811 | 7.2 |
| 18 | 31.3 | 8.1 | 91.8 | 0.1 | 0.8841 | 64.8 | 42.6 | 0.9 | 56.5 | 1.0907 | 6.5 |
| 19 | 42.4 | 9.0 | 90.9 | 0.1 | 0.8860 | 53.8 | 48.7 | 0.8 | 50.5 | 1.1040 | 6.8 |
| 20 | 54.3 | 11.9 | 87.9 | 0.2 | 0.8923 | 42.3 | 56.1 | 1.7 | 42.2 | 1.1199 | 5.9 |
| 21 | 68.6 | 17.3 | 82.5 | 0.2 | 0.9036 | 28.4 | 66.7 | 2.5 | 30.8 | 1.1427 | 4.9 |
| 22 | 9.5 | 9.7 | 90.1 | 0.2 | 0.8875 | 85.1 | 45.3 | 1.2 | 53.5 | 1.0966 | 5.8 |
| 23 | 20.5 | 10.5 | 89.3 | 0.2 | 0.8892 | 74.3 | 50.1 | 1.3 | 48.6 | 1.1070 | 6.0 |
| 24 | 32.0 | 12.4 | 87.4 | 0.2 | 0.8933 | 63.0 | 56.1 | 1.5 | 42.4 | 1.1198 | 5.7 |
| 25 | 44.4 | 17.4 | 82.4 | 0.2 | 0.9038 | 50.9 | 62.6 | 2.8 | 34.6 | 1.1339 | 4.5 |
| 26 | 61.1 | 26.1 | 73.8 | 0.1 | 0.9221 | 34.9 | 70.7 | 4.5 | 24.8 | 1.1513 | 3.4 |
| 27 | 9.6 | 14.0 | 85.7 | 0.3 | 0.8967 | 83.9 | 56.1 | 1.4 | 42.5 | 1.1198 | 5.0 |
| 28 | 21.4 | 20.7 | 79.0 | 0.3 | 0.9109 | 72.3 | 61.0 | 2.3 | 36.7 | 1.1304 | 3.7 |
| 29 | 34.8 | 25.8 | 74.0 | 0.2 | 0.9216 | 59.3 | 67.2 | 3.3 | 29.4 | 1.1438 | 3.2 |
| 30 | 52.6 | 37.6 | 62.2 | 0.2 | 0.9465 | 42.3 | 72.0 | 7.5 | 20.5 | 1.1542 | 2.3 |
| 31 | 7.6 | 21.1 | 78.6 | 0.3 | 0.9117 | 84.5 | 65.6 | 3.3 | 31.1 | 1.1403 | 3.9 |
| 32 | 19.5 | 29.8 | 69.9 | 0.3 | 0.9302 | 72.9 | 70.6 | 5.6 | 23.8 | 1.1512 | 2.9 |
| 33 | 39.3 | 52.2 | 47.5 | 0.3 | 0.9774 | 54.0 | 71.6 | 12.4 | 16.0 | 1.1533 | 1.6 |
| 34 | 1.9 | 40.1 | 59.2 | 0.7 | 0.9523 | 89.8 | 71.9 | 9.2 | 18.9 | 1.1540 | 2.2 |
| 35 | | | | | ← One Phase → | | | | | | — |
| 36 | | | | | ← One Phase → | | | | | | — |

EXAMPLES 37–44

Using the procedures described above for Examples 1–36, partition coefficients were determined for the extraction of 3-FTHF into water using the hydrocarbon solvents, decane, isooctane, p-xylene, and 1,3-diisopropylbenzene (DIPB). Partition coefficients also were determined by the same procedures for using the inert organic solvents 1-decanol (alcohol), isobutyl isobutyrate (ester, IBIB), 2,2,4-trimethyl-1,3-pentanediol monoisobutyrate (alcohol ester, TMPD-MIB), and dimethyl terphthalate (aromatic diester, DMT). The 3-FTHF:Solvent:Water volume ratios used in each of Examples 37–44 was 3:3:4. The partition coefficients are shown in Table VI wherein the values specified for 3-FTHF Solubility in Solvent are weight percentages, the values given for Temp are the temperatures (° C.), $K_{3FTHF}$ is the partition coefficient for 3-FTHF determined as described above and $K_{solvent}$ is the coefficient for the solvent utilized in each example determined form its solubility in the two phase and affected by the presence of the 3-FTHF substrate.

TABLE VI

| Example No. | Solvent | Density | 3-FTHF Solubility in Solvent | Temp | Partition Coefficients | |
|---|---|---|---|---|---|---|
| | | | | | $K_{Solvent}$ | $K_{3FTHF}$ |
| 18 | Toluene | 0.867 | 100 | 24.7 | 0.01165 | 6.518 |
| 37 | p-Xylene | 0.852 | 100 | 24.1 | 0.00740 | 7.022 |
| 38 | DIPB | 0.856 | 100 | 24.4 | 0.01904 | 5.869 |
| 39 | n-Decane | 0.730 | 0.93 | 25.1 | 0.00661 | 217.5 |

TABLE VI-continued

| Example No. | Solvent | Density | 3-FTHF Solubility in Solvent | Temp | Partition Coefficients | |
|---|---|---|---|---|---|---|
| | | | | | $K_{Solvent}$ | $K_{3FTHF}$ |
| 40 | Isooctane | 0.692 | 2.36 | 24.7 | 0.00746 | 73.91 |
| 41 | 1-Decanol | 0.829 | 100 | 25.7 | 0.01695 | 1.134 |
| 42 | TMPD-MIB | 0.937 | 100 | 24.4 | 0.00481 | 2.024 |
| 43 | IBIB | 0.844 | 100 | 24.2 | 0.00772 | 7.715 |
| 44 | DMT | 1.178 | 100 | 24.2 | 0.02526 | 2.218 |

EXAMPLES 45–56

Using the procedure described above for Examples 1–36, partition coefficients were determined for all solvents tested as well as for triphenylphosphine in toluene all extracted with water. In addition, the effect of 3-FTHF on the partition coefficient of toluene into water was explored by using different concentrations of aqueous 3-FTHF as the extraction medium. The results are summarized in Table VII wherein the CS:S Ratio is the Co-Solvent:Solvent volume ratio, the $H_2O:(S+CS)$ Ratio is the water:Solvent plus Co-Solvent, if any, volume ratio, DIPB, TMPD-MIB, and IBIB have the meanings given above, and DMP is dimethyl phthalate.

The purpose of the experiments of Examples 45–56 is to show the extent of partitioning of materials of limited water solubility into water and, by contrast, how 3-FTHF affects this partitioning. These examples include materials which could act as solvents for the reaction and extraction.

TABLE VII

| Example No. | Solvent | Co-Solvent | CS:S Ratio | H₂O:(S + CS) Ratio | Solvent Partition Coefficient |
|---|---|---|---|---|---|
| 45 | Toluene | — | — | 1:1 | 0.00063 |
| 46 | Toluene | 3-FTHF | 1:1 | 10:1 | 0.00865 |
| 47 | Toluene | 3-FTHF | 1:1 | 1:1 | 0.0117 |
| 48 | Toluene | 3-FTHF | 1:1 | 1:10 | 0.147 |
| 49 | Isooctane | — | — | 1:1 | 0.00002 |
| 50 | n-Decane | — | — | 1:1 | 0.00002 |
| 51 | p-Xylene | — | — | 1:1 | 0.00015 |
| 52 | 1,3-DIPB | — | — | 1:1 | 0.00006 |
| 53 | 1-Decanol | — | — | 1:1 | 0.00028 |
| 54 | TMPD-MIB | — | — | 1:1 | 0.00008 |
| 55 | IBIB | — | — | 1:1 | 0.00116 |
| 56 | DMP | — | — | 1:1 | 0.00731 |

EXAMPLE 57

The procedure described in the preceding examples was repeated using a 50:1 volume ratio of triphenylphosphine-:toluene and a 1:1 volume ratio of water:triphenylphosphine+toluene. The partition coefficient of triphenylphosphine between toluene and water was determined to be 0.00433.

EXAMPLE 58–61

Using t he procedure from Examples 1–36, the partition coefficient for 3-formyltetrahydrofuran between toluene and water was determined at several temperatures. The results are summarized in Table VIII wherein the 3-FTHF:Toluene and H20:FTHF+Toluene Ratios are by volume.

TABLE VIII

| Example No. | 3-FTHF: Toluene Ratio | H2O:(3-FTHF + Toluene) Ratio | Temp | 3-FTHF Partition Coefficient |
|---|---|---|---|---|
| 58 | 1:1 | 0.67:1 | 0.2 | 13.91 |
| 59 | 1:1 | 0.67:1 | 24 | 6.53 |
| 60 | 1:1 | 0.67:1 | 52.6 | 2.97 |
| 61 | 1:1 | 0.67:1 | 93.5 | 1.178 |

EXAMPLES 62–69

The hydroformylation product solutions produced in Reference Examples 2, 5, 10, 11, 12, 13, 14, 15, and 16 were subjected to aqueous extraction according to the present invention using a countercurrent extractor with an initial water to organic feed ratio of 0.6:1 (volume:volume) to recover the product. The primary extractor was a glass tube 2.5 inches in diameter and 48 inches in length having an internal volume of 3.5 liters and was packed with ¼ inch Penn State packing. The secondary extractor was a glass tube having a diameter of 1.375 inches and a length of 30 inches, an internal volume of 0.7 liter and also was packed with ¼ inch Penn State packing. The feed rates were 1–3 liters per hour. This extractor operated at an equivalent to three simple extractions. The temperatures in the extractor ranged from ambient (26.5° C.) to 43.7° C., indicative of the autogenous temperature rise associated with the extraction solvation/reaction. Cloudiness and sometimes a faint yellow color in the effluent from this extractor indicated incomplete separation of the aqueous from the solvent phase. The catalyst components remained in the reaction solvent phase. If any portion of this phase remained in or was not removed from the aqueous phase, it would contaminate the final product. Therefore, the aqueous phase obtained from the first extractor was subjected to a second countercurrent extraction with fresh solvent to remove this contamination. The feed ratio of aqueous phase to fresh solvent was 10:1 (volume:volume). The temperature gradient in the second countercurrent extractor was minimal since the heats of solvation/reaction accompanying the extraction had mostly emerged in the first extractor.

The results of these extractions are shown in Table IX wherein Solvent and Solv refer to the hydroformylation solvent component of the hydroformylation product solution used in each example, Isooct refers to isooctane, DIPB and TMPD-MIB have the meanings given above, DOP is bis(2-ethylhexyl)phthalate, HPS refers to hydroformylation product solution, Rh refers to rhodium, TPP refers to triphenylphospine, and FTHF refers to 2-and 3-FTHF. The values given for the HPS Components are weight percentages based on the total weight of the HPS and whose sum equals 100 percent, the values given for the components of the aqueous phase produced in the initial water (first) extraction of the HPS are the relative weight percentages determined by gas chromatographic analysis for the volatile organic components [solvent and FTHF], atomic absorption for the rhodium catalyst component, and P-31 nuclear magnetic resonance spectroscopy for the phosphine catalyst components (both the bound and free components). The reported numbers represent the total quantity of that material in that aqueous phase with 100 minus this value being the relative quantity of that material entering the other solvent phase. The values given for the components of the aqueous phase (second) produced by subjecting the first extraction aqueous phase to a second countercurrent extraction with fresh solvent are relative weight percentages determined by the same methods for each component. In this case, the reported numbers add up to the relative numbers from the first extraction with that relative number minus the second reported number being the quantity of that material going into the other solvent phase. Reporting the values in this manner gives the amount of that component in any phase by multiplying the amount in the HPS by the relative percentage of that component in any of the other phases. The purpose of these examples is to show the results of extracting actual reaction mixtures with water in order to compare them with other product recovery methods.

TABLE IX

| Aqueous Example No. | Solvent | HPS Components | | | | First Extraction Aqueous Phase Components | | | | Second Extraction Phase Components | | |
|---|---|---|---|---|---|---|---|---|---|---|---|---|
| | | Solv | Rh | TPP | FTHF | Solv | Rh | TPP | FTHF | Rh | TPP | FTHF |
| 62 | Toluene | 42.05 | 0.0046 | 0.0295 | 57.92 | 3.1 | 2.0 | 2.4 | 97.4 | 0.1 | 0.03 | 96.3 |
| 63 | Toluene | 42.00 | 0.0046 | 0.1413 | 57.85 | 3.3 | 1.8 | 2.6 | 98.2 | 0.1 | 0.05 | 97.0 |
| 64 | Toluene | 41.94 | 0.0092 | 0.2821 | 57.77 | 4.6 | 4.3 | 1.9 | 98.6 | 0.1 | 0.07 | 97.0 |

TABLE IX-continued

| Aqueous Example | | HPS Components | | | | First Extraction Aqueous Phase Components | | | | Second Extraction Phase Components | | |
|---|---|---|---|---|---|---|---|---|---|---|---|---|
| No. | Solvent | Solv | Rh | TPP | FTHF | Solv | Rh | TPP | FTHF | Rh | TPP | FTHF |
| 65 | Toluene | 41.82 | 0.0183 | 0.5626 | 57.60 | 2.9 | 1.4 | 2.2 | 98.1 | 0.06 | 0.06 | 97.3 |
| 66 | Isooct | 42.05 | 0.0046 | 0.0295 | 57.92 | 2.1 | 2.5 | 2.8 | 99.2 | 0.1 | 0.17 | 98.8 |
| 67 | DIPB | 42.05 | 0.0046 | 0.0295 | 57.92 | 3.5 | 0.4 | 1.9 | 97.7 | 0.05 | 0.02 | 96.0 |
| 68 | TMPD-MIB | 42.05 | 0.0046 | 0.0295 | 57.92 | 6.4 | 5.2 | 6.7 | 94.4 | 0.1 | 1.4 | 93.9 |
| 69 | DOP | 42.05 | 0.0046 | 0.0295 | 57.92 | 6.2 | 5.2 | 2.9 | 97.1 | 0.25 | 0.04 | 95.1 |

The invention has been described in detail with particular reference to preferred embodiments thereof, but it will be understood that variations and modifications can be effected within the spirit and scope of the invention.

I claim:

1. Process for producing an aqueous solution, essentially devoid of alkanol, containing a mixture of compounds having the formulas:

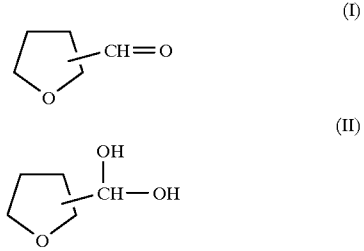

which comprises (1) intimately contacting a hydroformylation product solution comprising (i) 20 to 80 weight percent of an aldehyde of formula (I), (ii) hydroformylation catalyst components comprising rhodium and an organophosphorus compound, and (iii) 80 to 20 weight percent of a hydroformylation solvent with water essentially devoid of alkanol; (2) allowing the mixture of step (1) to separate into 2 phases; and (3) separating the 2-phases to obtain (a) a hydroformylation solvent phase containing catalyst components and (b) a water phase containing the compounds of formulas (I) and (II); wherein the volume ratio of water to hydroformylation product solution employed in step (1) is about 0.1:1 to 4:1; the hydroformylation product solution employed in step (1) contains less than about 15 weight percent of 2,5-dihydrofuran (2,5-DHF), 2,3-dihydrofuran (2,3-DHF), tetrahydrofuran (THF), or a mixture of any 2 or more thereof; and the mole ratio of compound (I) to compound (II) is about 0.05:1 to 20:1.

2. Process according to claim 1 wherein the hydroformylation solvent has a density in the range of about 0.6 to 0.9 and is selected from esters having about 6 to 20 carbon atoms, alkanes having about 5 to 20 carbon atoms, ketones having 6 to 20 carbon atoms, dialkyl ethers and cyclic ethers having 5 to 20 carbon atoms, alkyl-substituted benzenes having about 7 to 15 carbon atoms, tetrahydronaphthalene, and decahydronaphthalene.

3. Process according to claim 2 wherein the aldehyde of formula (I) constitutes about 50 to 70 weight percent of the total weight of the hydroformylation product solution.

* * * * *